United States Patent [19]

Gänshirt et al.

[11] Patent Number: 5,061,451
[45] Date of Patent: Oct. 29, 1991

[54] DEVICE FOR SEPARATING THE COMPONENTS OF A LIQUID, ESPECIALLY WHOLE BLOOD

[75] Inventors: Karlheinz Gänshirt, Dreieich; Wolfram Walker, Rödermark; Klaus D. Handel, Darmstadt, all of Fed. Rep. of Germany

[73] Assignee: NPBI Nederlands Produktielaboratorium voor Bloodtransfusieapparatuur en Infusievloeistoffen BV, Emmer-Compascuum, Netherlands

[21] Appl. No.: 344,336

[22] Filed: Apr. 27, 1989

[30] Foreign Application Priority Data

May 7, 1988 [DE] Fed. Rep. of Germany ....... 3815643

[51] Int. Cl.$^5$ .................. B01L 11/00; B01D 12/00
[52] U.S. Cl. .................................. 422/101; 210/86; 210/515; 210/782; 222/103
[58] Field of Search ............ 422/101, 294, 194; 210/86, 96.1, 97, 100, 103, 130, 515, 516, 523, 744, 745, 782, 927; 222/703, 95, 96; 604/4, 5, 6, 132, 154, 155

[56] References Cited

U.S. PATENT DOCUMENTS

| 4,228,926 | 10/1980 | Gordon | 222/103 |
| 4,284,209 | 8/1981 | Barbour, Jr. | 222/103 |
| 4,350,585 | 9/1982 | Johansson et al. | 210/97 |
| 4,608,178 | 8/1986 | Johansson et al. | 210/744 |
| 4,753,739 | 6/1988 | Noble | 210/787 |
| 4,807,676 | 2/1989 | Cerny et al. | 604/6 |
| 4,909,949 | 3/1990 | Harmony et al. | 210/787 |

Primary Examiner—Robert J. Warden
Assistant Examiner—Theresa A. Trembley
Attorney, Agent, or Firm—Sprung Horn Kramer & Woods

[57] ABSTRACT

A device for obtaining from at least two spatially separated areas the heterogeneous components of a liquid, especially stabilized whole blood in a flexible and transparent bag with at least one line leading out of it. The device consists of a front plate that is part of a housing, of a pressure-application plate that pivots toward the front plate, of a drive mechanism, and of a sensor. The point that the pressure-application plate pivots around is below the bag and at the point of intersection between the surfaces of the plates, specifically at least 30% of the length of the pressure-application plate away, and the drive mechanism engages a lever that is rigidly secured to the pressure-application plate. A bag employed in conjunction with the device has an intake line at the top and an outlet line and a filling and blood-collecting tube at the bottom, only one bag-to-bag transport system at the top, and no outlet connections.

8 Claims, 3 Drawing Sheets

DEVICE FOR SEPARATING THE COMPONENTS OF A LIQUID, ESPECIALLY WHOLE BLOOD

BACKGROUND OF THE INVENTION

The invention concerns a device for obtaining one after another and from at least two spatially separated areas the components of a liquid, especially stabilized whole blood contained in a flexible bag with at least one line leading out of it.

In the devices that have been available up to now for separately obtaining the components of a liquid, especially whole blood in centrifuged bags, the bag containing the liquid or whole blood is squeezed between a perpendicular and stationary plate and another plate that is hinged to the bottom of the first and can be pivoted toward it.

The requisite force is obtained with springs. These devices, conventional plasma squeezers, have considerable drawbacks, however. First, the squeezing procedure must be constantly monitored and decelerated or terminated once a particular layer of components has been attained at the upper edge. Second, since the force of the springs decreases while the bag is being squeezed, greater force than can be obtained from the springs alone must be exerted to squeeze a more viscous layer, the Buffy-coat layer for instance, out of the blood. Layers of that type can usually be obtained only by adding manual force. Finally, only bags with an outlet at the top can be employed in these devices.

The conventional plasma squeezers have been improved by the addition of a cell sensor, making it unnecessary to monitor the squeezing procedure. The inhomogeneities in pressure due to the use of springs, however, are still present along with the associated drawbacks.

A considerable improvement in the aforesaid devices has been attained with automatic drive mechanisms.

German OS 3 012 228 describes a device wherein the pressure is applied hydraulically, pneumatically, or hydropneumatically. Sensors for determining the various component layers allow automatic squeezing.

German OS 3 417 892 also describes an automatic device wherein the squeezing structure is accommodate between an upper and a lower pressure-application plate, requiring three separately operated pressure-application structures.

The stationary plate and the moving plate are parallel in both devices, and the bag must accordingly be manually secured between the plates until the squeezing procedure is initiated and it can be secured by the commencing pressure. Since the bag is teardrop-shaped, however, it will rapidly deform and create turbulence in the interface between its contents, making it more complicated to squeeze out a pure layer of component. Since the force exerted on the stationary plate is relatively high (approximately 50 kp), the plates must be relatively strong.

OBJECT OF THE INVENTION

The object of the invention is accordingly to improve a device of the aforesaid type for separately obtaining the components of a liquid to the extent that the bag does not need to be manually secured and will not rapidly deform initially, preventing the centrifuged layers from mixing together again. The pressure will also be applied automatically and continuously. Use of appropriate sensors and of a bag with at least one and preferably two outlet lines will on the whole result in a rapidly and efficiently operating and simple device for obtaining pure blood preparations in particular.

This object is obtained in accordance with the invention in a device for obtaining from at least two spatially separated areas the heterogeneous components of a liquid, especially stabilized whole blood in a flexible and transparent bag with at least one line leading out of it and consisting of a front plate 1 that is part of a housing 11, of a pressure-application plate 2 that pivots toward the front plate, of a drive mechanism, and of a sensor, by the improvement wherein the point 3 that the pressure-application plate pivots around is below the bag and at the point of intersection between the surfaces of the plates, specifically at least 30% of the length of the pressure application plate away, and the drive mechanism engages a lever 12 that is rigidly secured to the pressure-application plate.

The essential feature is that the stationary plate and the pressure-application plate are not parallel but initially at an angle to each other and that the pivoting point is in the aforesaid specific location. The bag can accordingly be adequately secured before any pressure is applied just be placing it in the device and will not rapidly deform as the squeezing procedure commences. The more extensive cross-section at the top of the bag will also considerably eliminate interface turbulence toward the end of the procedure as compared to what occurs with parallel plates. The multiple bag-to-bag communication system, the break-off section for example, at the top will also be much easier to remove than it is when the plates are parallel because of the wider opening. Since the pressure-application plate is approximately 30% shorter than the stationary plate, it is possible to use bags with another outlet line at the bottom. The automatic operation provided by the drive mechanism that is rigidly secured to the pressure-application plate by way of a lever and by the associated sensors in the device in accordance with the invention make it possible to obtain pure blood preparations for example efficiently, simply, and rapidly.

The scanner can be an optical detector 4 or 10 that activates a mechanism 9 that blocks off at least one of the outlets when a specific component layer attains a prescribed level in the bag.

The optical detector 4 can be positioned on the front plate in the vicinity of the bag.

The optical detector 10 can be positioned in the vicinity of the tubing.

The device can also have a limit switch.

The drive mechanism can be hydraulic or electric.

The drive mechanism can be positioned on the front plate.

A pressure sensor 5 can be positioned in the center of the front plate.

The bag employed in conjunction with the device in accordance with the invention can have an intake line 13 at the top and an outlet line 14 and a filling and blood-collecting tube 15 at the bottom, only one bag-to-bag transport system at the top, and no outlet connections.

BRIEF DESCRIPTION OF THE DRAWING

The invention will now be described in detail with reference to the drawing, wherein.

DETAILED DESCRIPTION OF THE INVENTION

Figure 1:
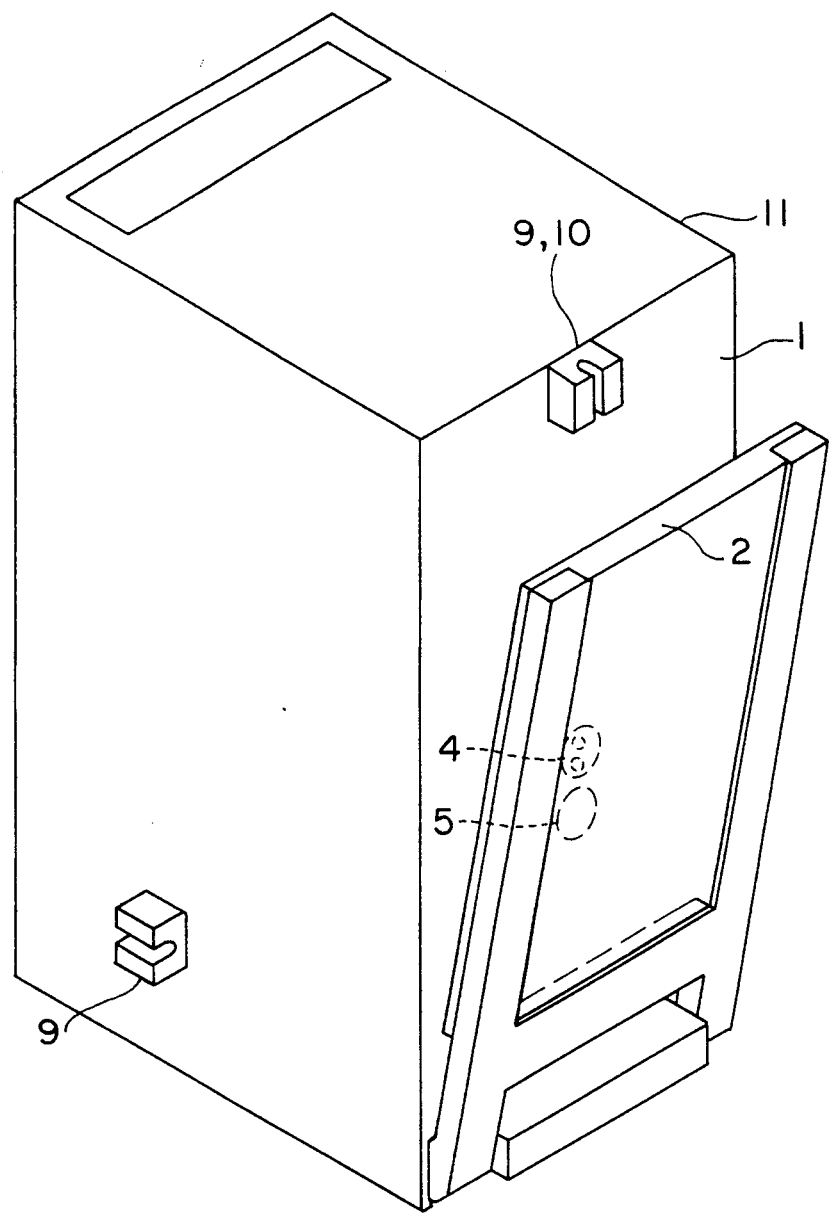
FIG. 1 is a front perspective view, FIG. 2 a side view of a preferred embodiment of the device.

The device in accordance with the invention consists of a housing 11 that accommodates the drive mechanism and has a stationary front plate 1 and a pressure-application plate 2 that is initially at an angle to the front plate. The pressure-application plate can be made of plastic and is secured in a metal frame. The line of intersection between the surfaces of the two plates is approximately 30% of the length of pressure-application plate 2 below the bag. Positioned on the line of intersection and about 30% below the length of pressure-application plate 2 or of the bag is the point 3 that the pressure-application plate pivots around. This arrangement allows the additional tubing connections characteristic of such bags as the one described in European Patent 8 611 079.9, with more than one outlet, one at the top and one at the bottom for example, to be secured in the space between the pivoting point 3 and the bag preventing them from impeding complete compression of the bag.

Lowering the point 3 that pressure-application plate 2 pivots around farther below the bag in accordance with the invention than it is in known devices reduces the powerful deformation of the bag at the beginning of the squeezing procedure and considerably decreases turbulence at the interface.

The angle between the two plates keeps the bag in a constant position. The upward flow of the lighter-weight components will be reduced due to the wider cross-section at that point of the bag, and much less of the heavier components will be entrained.

The drive mechanism is rigidly connected to pressure-application plate 2 by way of a lever 12. Pressure-application plate 2 is set in motion by electric or hydraulic force for example. The drive mechanism, which consists of a motor 6, a transmission 7, and a spindle 8, is preferably positioned on front plate 1, ensuring that approximately the same force will be exerted on front plate 1 from outside and from inside, and it is accordingly exposed only to torques that are less than those to which the device on the whole is subjected. The weakness of these forces makes it possible to keep front plate 1 thin because it does not need to be especially strong.

The sensors can be tubing detectors 10 of the type described in GB Patent 1 537 096 or a detector 4 positioned in the center of the front plate. An interface can accordingly be detected as it rises during the squeezing procedure and associated tubing clamps 9 tightened as soon as one component has been squeezed out.

The device in accordance with the invention can also be equipped with a pressure sensor 5 positioned below bag detector 4 on front plate 1 and controlling the drive mechanism. This system will ensure constant compression, which will be automatically decreased if an outlet line becomes obstructed to prevent undesirable excess pressure.

The device being claimed can also be equipped with a limit switch that will activate the device's clamp or clamps once the plates are separated by a prescribed distance or once the bag has been emptied to a prescribed level.

The embodiment just described is especially appropriate for bags with an upper and a lower exit. An interface detector controls the upper clamp. It can be positioned on front plate 1 in the vicinity of the bag or in the vicinity of the tubing. If a bag detector 4 is employed, the upper clamp is closed as soon as it detects the rise of the interface from the more rapid outflow of the lighter-weight component. The heavier component will then flow down and the interface will descend again. As soon as the detector determines that the interface is at a particular level, the upper clamp will be opened again. This process will maintain the interface at a level defined by bag detector 4 throughout the squeezing procedure. Once the plates are at a certain distance from each other or once the bag has been emptied to a certain extent, the clamp or clamps are closed and the procedure is over.

When a tube detector 10 positioned at the top of the tube is employed, the upper clamp is closed once all the lighter-weight component has been squeezed out. The heavier component is squeezed out until the plates are at a prescribed distance apart or the bag has been emptied to a prescribed extent.

Figure 2:
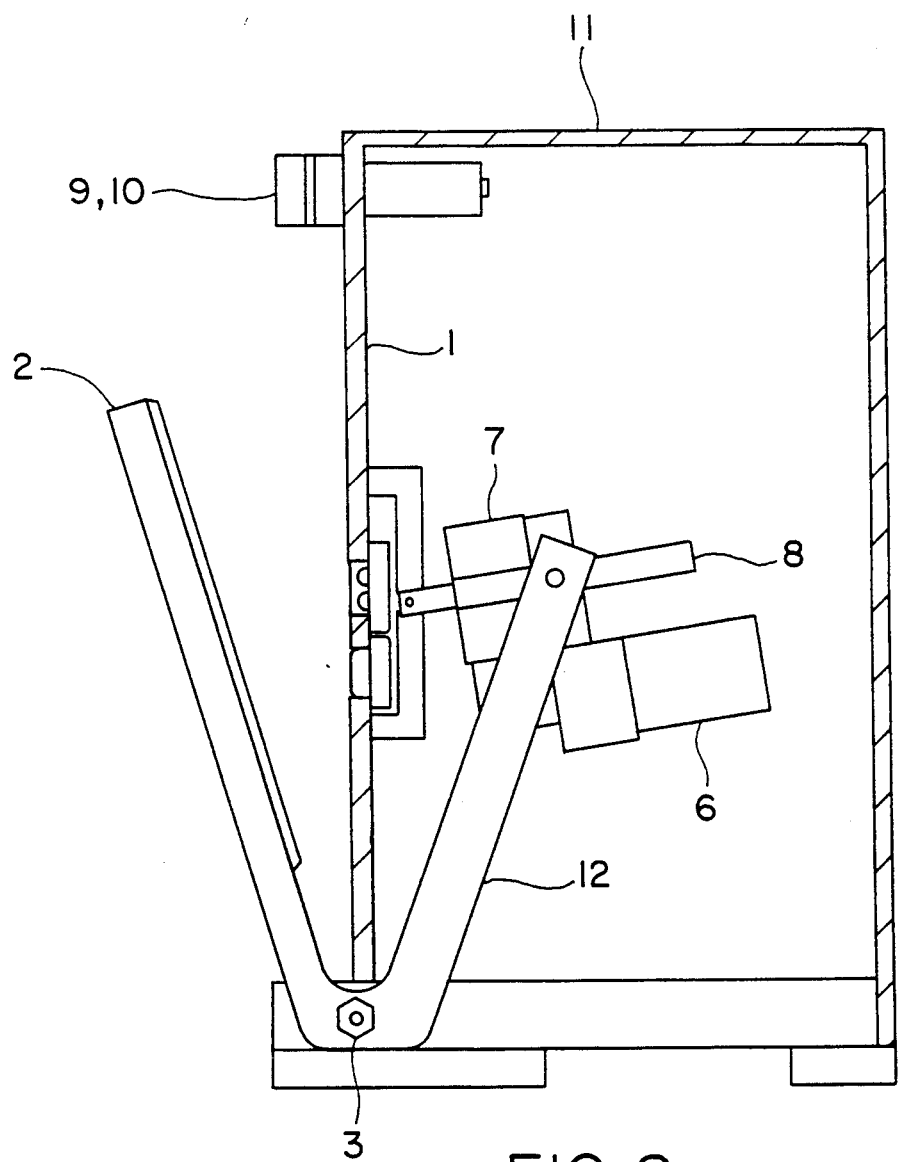

FIG. 2 is a side view of the device in accordance with the invention.

The drive mechanism is accommodated in a housing 11 with a front plate 1. Motor 6 and transmission 7 are fastened to front plate 1 by spindle 8 and rigidly secured to pressure-application plate 2 by lever 12. Accommodated in the center of front plate 1 is a bag detector 4 with a pressure sensor 5 below it. At the top of front plate 1 are tube clamps 9 and a tube detector 10.

Pressure-application plate 2 is more than 30% shorter than front plate 1. The line of intersection between the surfaces of the plates and the point 3 that pressure-application plate 2 pivots around are accordingly below the bag.

The bag that contains the fluid, preferably a bag with two outlet lines, is positioned in accordance with the invention between the two plates such that the space below it remains free and can be used for the second outlet line without impeding the squeezing procedure.

Figure 3:
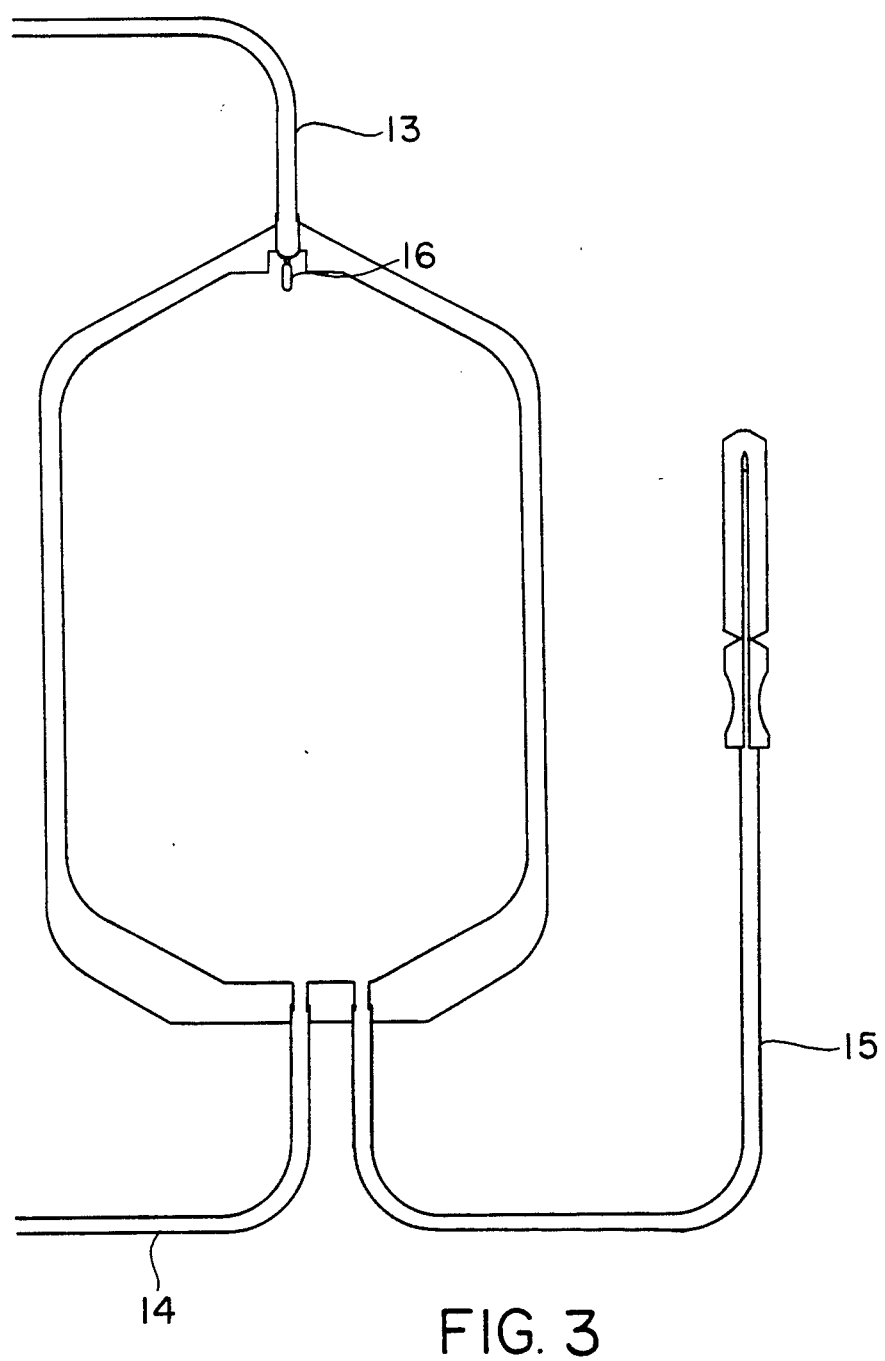
FIG. 3 illustrates a bag that is especially preferred for use with the device in accordance with the invention.

The bag illustrated in FIG. 3 has an upper intake line 13 and a lower outlet line 14. It contains no connections and only one bag-to-bag transport system, breakoff section 16 for example, which is at the top.

Outlet line 14 is at the same end of the bag as a filling and blood-collecting tube 15.

This bag design ensures that break-off section 16 will always be at the top during the centrifuging process and cannot break of prematurely. The layers separated by the centrifuging will not become turbulent when the section is broken off, as might easily happen if it were at the bottom. Furthermore, no undesired blood cells will be retained at the top of the bottle as might happen if there were a connection at that point. Furthermore, contamination at the top of the bottle is prevented for the same reason, because filling and blood-collecting tube 15 is at the opposite end along with outlet line 14.

This type of bag can as previously described herein simply be placed in the device in accordance with the invention and completely squeezed out.

One essential advantage of the device being claimed herein is that, since pressure-application plate 2 is shorter than front plate 1, a DIN-standard bag that is filled to a specific level can always be inserted in the same position. It will be unnecessary to hold it in place manually until the squeezing procedure begins as it is when the two plates are parallel. Furthermore, the initial rapid deformation of the bag and the concomitant undesired interface turbulence are considerably decreased. Making pressure-application plate 2 shorter than front plate 1 in accordance with the invention ensures that the bag will be squeezed completely empty unimpeded by extra outlet lines as would happen with bags with outlets at the top and bottom.

The more extensive cross-section at the top of the bag in accordance with the invention also reduces the risk of interface turbulence toward the end of the squeezing procedure.

The force exerted on front plate 1 as the bag is squeezed out is, in contrast to systems employing parallel plates, compensated in that the position of the drive mechanism ensures that the force exerted on the plate from outside will equal the force exerted on it from inside. Thinner plates can accordingly be employed.

The device in accordance with the invention can for example be employed for separately obtaining whole-blood components in leukophoresis, plasmaphoresis, thrombophoresis, etc., which preferably employ bags with more than one outlet line.

It is understood that the specification and examples are illustrative but not limitative of the present invention and that other embodiments within the spirit and scope of the invention will suggest themselves to those skilled in the art.

What is claimed is:

1. A device for obtaining from at least two spatially separated areas the heterogeneous components of a liquid, in a flexible bag with at least one outlet and a line leading out of it, the device comprising a housing including a front plate, a V-shaped lever pivotable about an axis adjacent the bottom of the housing and comprising two arms of which one is inside the housing and one is outside the housing, a pad on the outside arm of the lever facing the housing front plate, based on the length of said outside arm said pad terminating a distance of about 30% from the axis, and a drive mechanism operatively connecting the inner arm of said lever with the front plate of the housing.

2. A device as in claim 10, including a sensor which activates a mechanism that blocks off at least one of the outlets from the bag when a specific component layer attains a prescribed level in the bag.

3. A device as in claim 2, wherein the sensor is an optical detector positioned on the front plate in the vicinity of the bag.

4. A device as in claim 2, wherein the sensor is an optical detector positioned in the vicinity of the tubing of a bag when in operative position.

5. A device as in claim 1, including a limit switch.

6. A device as in claim 1, wherein the drive mechanism is hydraulic or electric.

7. A device as in claim 1, wherein the drive mechanism is positioned on the front plate.

8. A device as in claim 1, wherein a pressure sensor is positioned in the center of the front plate.

* * * * *

UNITED STATES PATENT AND TRADEMARK OFFICE
CERTIFICATE OF CORRECTION

PATENT NO. : 5,061,451

DATED : October 29, 1991

INVENTOR(S) : Ganshirt et al.

It is certified that error appears in the above-identified patent and that said Letters Patent is hereby corrected as shown below:

Col. 6, line 12   Delete " claim 10 " and substitute -- claim 1 --

Signed and Sealed this

Twenty-seventh Day of April, 1993

Attest:

MICHAEL K. KIRK

Attesting Officer

Acting Commissioner of Patents and Trademarks